US00PP09124P

United States Patent [19]

Johnson

[11] Patent Number: Plant 9,124

[45] Date of Patent: May 2, 1995

[54] ROSEMARY PLANT NAMED 'RENZELS'

[76] Inventor: Philip A. Johnson, 360 Marshall Dr., Walnut Creek, Calif. 94598

[21] Appl. No.: 226,999

[22] Filed: Apr. 13, 1994

[51] Int. Cl.[6] ..... A01H 5/00

[52] U.S. Cl. ..... Plt./54.1

[58] Field of Search ..... Plt. 54.1

*Primary Examiner*—James R. Feyrer

[57] ABSTRACT

A new cultivar of *Rosmarinus officinalis* plant named 'Renzels' characterized by its unique combination of rich blue-violet flowers on a shrub that exhibits great vigor and an extremely prostrate habit.

1 Drawing Sheet

BACKGROUND OF THE INVENTION

The invention relates to a new and distinct variety of the Labiatae family which has been named *Rosmarinus officinalis* 'Renzels' by the inventor, and more particularly to a rosemary shrub that possess a low and prostrate habit, good vigor and flowers of a rich blue-violet, and which qualities give it great value as an ornamental shrub in the landscape trade.

Certain clones of the shrub rosemary have long been in cultivation, being appreciated for their scent, flavor, hardiness and beauty. In California, it is a major market plant in the landscape trade, particularly for its drought resistance, deer resistance, good form, pleasing flowers, resistance to pests and diseases, and ease of pruning. One of the most popular clones, *Rosmarinus officinalis* 'Prostrata', is described as being introduced to Great Britain in 1900 (W. J. Bean; 8th Ed.). Its habit is ". . . prostrate, making a curtain over the edge of walls, attaining a height of 2 ft. and spread of 4–8' and having pale blue flowers." (Sunset Western Garden Book, 1990). The typical R.o. 'Prostrata' available in the landscape trade has a flower color of RHS 92C-92D. My selection has a rich blue-violet flower with similar prostrate habits and which sets it apart from other clones of *Rosemary officinalis.*

Another clone, *Rosemary officinalis* 'Collingwood Ingram' (syn: 'Benendon Blue', *R. Ingramii*) was introduced to Great Britain in 1933 (W. J. Bean; 8th Ed.) and is described as being a ". . . tallish bank or ground cover with high color value, 2–2½ ft. tall and 4' or more wide, with branches that curve gracefully and with flowers of a rich, bright blue violet (Sunset Western Garden Book, 1990). A clone of R.o. 'Collingwood Ingram', reportedly a sport that exhibited a more prostrate habit, was introduced into the nursery trade. This clone, *Rosmarinus officinalis* 'Ken Taylor', has been generally available in the nursery trade in Northern California for the past 10 years, but is still not widely known. It has been described as having ". . . weaker branches than the original and trails more like 'Prostratus' down banks and walls. The leaves are the same lustrous dark green, and the flowers are the same bright lavender blue, as the original." (Wintergreen Nursery Catalog, Watsonville, Calif., 1993). Another nursery in the Watsonville area of California describes R.o. 'Ken Taylor' as being ". . . very close to 'Benendon Blue', maybe slightly lower. Dark blue flowers." (Monterey Bay Nursery Catalog, 1992). To this inventor's eye, through experience in the landscape business, R.o. 'Ken Taylor' exhibits a general upright growth in the center with side branches being arching to decumbent, making in time a high centered mount with side branches that tend to arch rather than drip over walls.

The invention 'Renzels' rosemary possesses a number of attributes that caused it to be selected for trail and which are believed to indicate a promising commercial life, and which attributes set it apart from other clones available in the landspace trade. This invention relates to a new and distinct selection of *Rosemary officinalis* by exhibiting a truly prostrate habit with flowers of a rich blue violet which retaining qualities typical of the species such as ease of propagation and cultivation, ability to grow where environmental conditions are tough, hardiness, deer resistance, resistance to pests and diseases, and ease of pruning. It is intended to market this plant under the name Trademark 'Irene'.

ORIGIN AND ASEXUAL REPRODUCTION OF THE INVENTION

The invention 'Renzels' was discovered by this invention in the winter of 1991 growing in the crack of a dry stack retaining wall this inventor had built 7 years previous in a garden in the town of Orinda, Calif., (USDA zone 8). While it cannot be known with certitude, it is strongly believed to this inventor's eye that it is a voluntary F1 seedling between *Rosemary officinalis* 'Prostrata' and *Rosemary officinali* 'Ken Taylor', as the site where found contained plantings of both plants. Notice was taken because of its ability to grow in a very hot, dry, south facing exposure, its prostrate habit, and its flowers of a rich blue-violet. Semi-hardwood cuttings, some of which had rooted at the nodes, were taken by this inventor and rooted in a terrarium in an unheated greenhouse in Walnut Creek, Calif. Rooting was routine, and its ease will enable one of ordinary skill to make use of the invention. Second and subsequent generation cuttings were taken, and all subsequent plants have exhibited the characteristics of the mother plant.

SUMMARY OF THE INVENTION

The new variety of *Rosmarinus officinalis,* named 'Renzels' is characterized as to novelty by producing flowers of a blue-violet, RHS Color Chart 94C-94D, of 12–16 mm in size, on a plant that exhibits a prostrate habit, which plant has value as an ornamental plant in the landscape and garden industries. The novelty of the plant is not dependent on traits it exhibits no different in this inventor's eye than those of its parents and others of the species in regards to ease of propagation and cultivation, ability to grow where environmental conditions are tough, hardiness, deer resistance, resistance to pests and diseases, and ease of pruning. Foliage color of the new invention 'Renzels' rosemary ranges from medium to dark green (RHS Color Chart Green Group 137A-137B) but is not particularly distinct from the species. Fragrance of foliage is of a medium rosemary fragrance, and is not substantially different than the foliage fragrance of its presumed parents.

BRIEF DESCRIPTION OF THE DRAWINGS

The top drawing is a photo of the original plant of *Rosmarinus officinalis* 'Renzels' in situ. Color of the inflorescence has been matched in the photo lab to actual samples of the flowers. Color correction is meant to convey the true flower colors and not the foliage color, as this trait is not of novelty.

The middle drawing is a photo of a stem of *Rosmarinus officinalis* 'Renzels' on the left and a stem of *Rosmarinus officinalis* 'Prostrata' on the right. Color of the inflorescence has been matched in the photo lab to actual samples of the flowers. Color correction is meant to convey the true flower colors and not the foliage color, as this trait is not of novelty.

The bottom drawing is a photo of a of a 9 month old plant of *Rosmarinus officinalis* 'Renzels' in Lafayette, Calif., exhibiting its prostrate habit. Color of flower and foliage is close to true, but is not meant to convey the same information as the upper 2 drawings as to true colors.

DETAILED PLANT DESCRIPTION

Referring more specifically to morphological details of this new and distinct variety of rosemary shrub, named *Rosmarinus officinalis* 'Renzels' the following has been observed under the ecological conditions prevailing in sites in Orinda, Lafayette, and Walnut Creek areas of California (USDA Zone 8, Sunset Zone 14). These conditions ranged from hot, sunny exposed sites with both good and poor soils to sites with partial shade and severe tree root competition. All major color code designations are by reference to the Royal Horticultural Society Colour Chart, 1966 Edition. Common color names are also employed occasionally.

Overall size and habit: Spreading shrub with numerous decumbent side branches. Certain specimens observed after 2 years attained a height in the center of about 12" and spread of 3–4'. While the period of time for evaluation purposes is only 2 years, and ultimate size cannot be proven, the 'Renzels' rosemary exhibits in habit characteristics of its probable parent, R.o. 'Prostrata' and is believed to be comparable in terms of ultimate size and spread. No particularly severe diseases or pests have appeared to affect test plants or the original plant. Intermode lengths of the 'Renzels' rosemary are substantially equal to those of the species. The prostrate habit of the stems and their ability to literally drip over the edges of walls, combined with the 'Renzels' rosemary's bright flower color results in a plant with more attractive appointment where it is used for landscape purposes, as compared with other members of the species.

Vigor: In a planting in Lafayette, Calif., plants planted out from 3" with an average 6" across dimension attained a terminal growth rate of 12" to 36" for the period of June 1993 to March of 1994. Terminal growth of specimens of this plants in average soil conditions without tree root competition averaged 18–24" between June 1993 and March 1994. The 'Renzels' exhibits in general in excellent vigor.

Tolerance to drought: Long term ability to withstand drought is not provable at this time. However, it is estimated that the 'Renzels' Rosemary's ability to withstand drought should not be substantially different than the species.

Hardiness: *Rosemary officinalis* 'Renzels' is hardy in the Western Contra Costa County area of California (USDA Zone 8, Sunset Zone 14). Ultimate cold hardiness has not been observed, but it is estimated to not be substantially different than other members of the species. Heat tolerance is excellent.

Flowers: In Northern California, in Contra Costa County, USDA Zone 8, Sunset Zone 14, 'Renzels' rosemary flowers in the late winter and early spring. As with the species, it will usually flower less heavily in the fall, and is known in moderate winters to have flowers throughout the winter. The flower parts of the plant of this disclosure, *Rosemary officinalis* 'Renzels' are substantially identical to those of the species per se.

*Arrangement.*—Flowers produced in clusters of two or three in the leaf axils of the previous season's shoots, arranged in short axillary racemes.

*Shape.*—Calyx campanulate, 2 lipped; corolla longer than calyx, 2 lipped, upper lip strongly concave, 2-lobed; lower lip 3-lobed with concave middle lobe, fertile stamens 2, exerted, style long, incurved, unbranched; Calyx has color on upper sides of grey-purple group 187A, light green to white below. Buds are of the same color.

*Size.*—Length 12–16 mm; pedicels 4–6 mm.

*Color.*—As seen from a distance of 3', flowers blend into a color that fits RHS 94C-94D. Color of upper two lobed petal ranges from off white in a narrow band along the mid rib, transitioning to a mid blue violet, 94D, in the center, and having the darkest saturation of color RHS 94B at the margins. Many dark splotches (less than 1 mm long) occur in the central part of the petal and fade out towards the edge of the flowers. These splotches are of RHS color violet blue 89C. The lower three lobed petal has little to non-existent splotching and the petal is of a more uniform saturated color RHS 94C-94D, with more saturation occurring at the margins. Stamens and style are blue violet 94C-94D. Color of the flowers may vary slightly due to weather conditions or exposure; lighter in hot, dry, sunny conditions, and deeper in cooler and shadier conditions.

*Pedicels.*—Average 4–6 mm in length. Color is of grey-purple group 187A. The same color occurs on the stem in the immediate areas of pedicel attachment.

Leaf:

*Arrangement.*—The coloration of the new and mature foliage of 'Renzels' rosemary is substantially identical to that of companion plants of the species. Leaves opposite, linear, not stalked. Leaves aromatically fragrant when crushed. Leaf coloration of this plant has been observed under sunny conditions in Walnut Creek, Calif. It is assumed that a certain amount of color variation will occur under different growing conditions, as occurs in other members of the species. Novelty of the patent is not dependant on leaf coloration.

*Size.*—5–25 mm long; 2–5 mm wide.

*Color.*—Glossy green above RHS 137A-137B, white-hairy below. Color of foliage tends towards the darker green of its supposed parent, R.o. 'Ken Taylor'.

*Shape.*—Narrow, entire, blunt at the apex, margins recurved.

Stems: Older stems are of a dark brown color RHS Brown Group Group 200 D. Newer stem growth is whitish pubescent to light green, RHS 145C-145D. Stems are slightly arching in the center and decumbent on the perimeter of the plant, heavily clothed with short axillary stems 5–20 mm long occurring in almost every leaf axle. Side branching occurs oppositely along the stems with leaf intermodes being 10–20 mm. Stems exhibit an ability to readily root at the nodes.

Fruit: Fruit of 4 glabrous nutlets. Seeds produced by the plant of this disclosure are substantially identical to those produced by typical specimens of the species in terms of size and appearance. Fertility of the seeds has not been established.

I claim:

1. A new and distinct variety of rosemary plant as substantially shown and described herein, that is characterized particularly as to novelty by the unique combination of its extremely prostrate habit and rich blue-violet flowers.

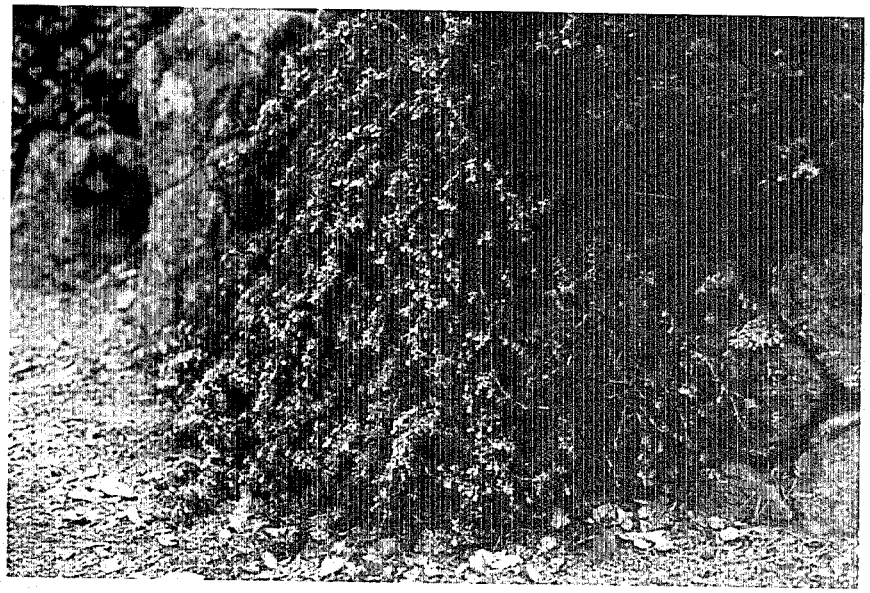
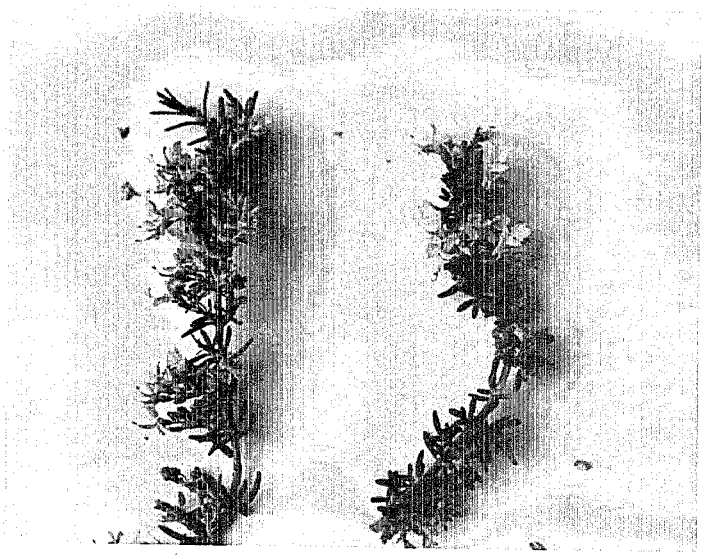
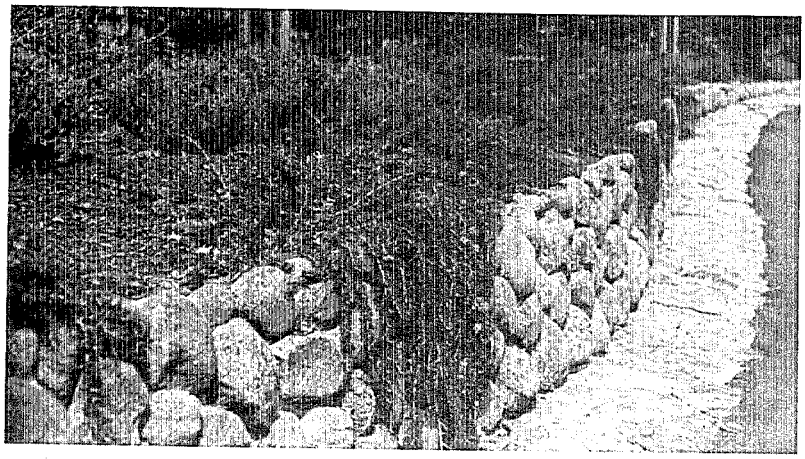

* * * * *